United States Patent
Simon et al.

(12)

(10) Patent No.: US 6,191,071 B1
(45) Date of Patent: Feb. 20, 2001

(54) PLANT-TREATMENT AGENTS

(75) Inventors: Joachim Simon, Düsseldorf; Hanns Peter Müller, Odenthal; Uwe Priesnitz, Solingen; Hans-Georg Rast, Bergisch Gladbach, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/297,628

(22) PCT Filed: Oct. 27, 1997

(86) PCT No.: PCT/EP97/05932

§ 371 Date: May 4, 1999

§ 102(e) Date: May 4, 1999

(87) PCT Pub. No.: WO98/19531

PCT Pub. Date: May 14, 1998

(30) Foreign Application Priority Data

Nov. 7, 1996 (DE) .............................................. 196 45 842

(51) Int. Cl.[7] .......................... A01N 25/10; A01N 37/34; A01N 43/40; A01N 43/50; A01N 43/653

(52) U.S. Cl. .......................... 504/310; 504/360; 514/341; 514/383; 514/772.3

(58) Field of Search .................... 504/360, 310; 514/772.3, 341, 383

(56) References Cited

U.S. PATENT DOCUMENTS

| | | | | |
|---|---|---|---|---|
| 4,405,360 | * | 9/1983 | Cardarelli | 71/117 |
| 5,326,777 | * | 7/1994 | Ludwig et al. | 514/383 |
| 5,644,020 | * | 7/1997 | Timmermann et al. | 528/288 |

* cited by examiner

*Primary Examiner*—S. Mark Clardy
(74) *Attorney, Agent, or Firm*—Joseph C. Gil

(57) ABSTRACT

The invention concerns novel plant-treatment agents comprising: at least one thermoplastically processable biodegradable polyester amide, optionally in a mixture with one or a plurality of further thermoplastically processable, biodegradable polymer components; at least one agrochemical substance; and optionally additives. The invention further concerns a process for preparing these agents, and their use in the application of agrochemical substances.

9 Claims, No Drawings

PLANT-TREATMENT AGENTS

TECHNICAL FIELD OF THE INVENTION

The present invention relates to novel plant-treatment compositions based on biodegradable polyester amides containing active compounds, to a process for their preparation and to their use for applying agrochemically active compounds.

BACKGROUND OF THE INVENTION

Numerous thermoplastically processable polymers which contain agrochemically active compounds and can be used in crop protection have already been disclosed (cf. DE-A 4 002 736, U.S. Pat. No. 4,743,448, U.S. Pat. No. 4,666,767 and U.S. Pat. No. 5,201,925). However, these systems have the disadvantage that it is a priori unforeseeable whether a sufficient amount of the active components is released over a sufficiently long period of time. Moreover, after the end of the treatment, polymers and active compound residues remain in the soil or on the plants where they are undesirable and have to be disposed of in a costly manner.

Furthermore, polymeric carrier materials have been disclosed which are partially or completely degraded hydrolytically, during or after their application, by enzymes and/or by microorganisms (cf. Envir. Sci. and Techn. 7 (1973), 955, Coat Plast. Chem. 42 (1980), 436–440, Proc. Int. Symp. Contr. rel. Bioact. Mat. 12 (1985), 179, J. Appl. Pol. Sci 28 (1983), 327–334, "Biomaterials", Thieme Verlag, Stuttgart-New York, 1987, pages 1–65, Chem. Soc. 1990, 127–148, Chem. Pharm. Bull. 37 (1989), 1954–1956 and Macromolecules 23 (1990), 26–31). Suitable substances for such systems are, for example, polylactic acids and copolymers thereof, polycaprolactone and also polyhydroxybutyrates and copolymers thereof. However, these polymers have hitherto either been unsuitable for an economical formulation of agrochemically active compounds, or the active compounds were not released in a satisfactory manner.

In addition, numerous other biodegradable preparations composed of carrier materials and agrochemically active compounds have been described which release the active components under the application conditions. Thus, suitable carrier substances are, for example, hydrophilic polymers based on polysaccharides, such as starch, into which water-insoluble polymers are incorporated in the form of blends, for mechanical stabilization and to regulate the release of active compounds (cf. Biomaterials 10 (1989) 400–412). However, the biological degradability of these preparations leaves a great to be desired, as does the cost of producing them (cf Study of the European Commission Directorate General XII, EUR 16 102 EN).

It is furthermore possible to use destructured hydrophilic polymers in combination with at least one water-insoluble, synthetic and thermoplastic polymer as carrier substances for active compounds (cf. EP-A 0 344 118). Likewise, it is possible to use blends based on biodegradable starch and synthetic polymers containing at least one free carboxyl group for the abovementioned purpose (cf EP-A 0 404 727). However, it is disadvantageous that in each case only the hydrophilic polymer components are biodegraded, while the other polymer components remain as undesirable residues.

Finally, it has also been disclosed that fibres based on polyhydroxyalkoxides and polysaccharides or copolymers based on tartaric acid and/or lactic acid can act as carriers and/or matrix for active compounds (cf. EP-A 0 132 299, EP-A 0 253 490, EP-A 0 126 827 and DE-A 3 936 191).

However, it is unfavourable that the incorporation of the active compounds causes problems, or that the degradability or the release of the active compounds is not always unsatisfactory.

DETAILED DESCRIPTION OF THE INVENTION

This invention, accordingly, provides novel plant-treatment compositions, consisting of
  at least one thermoplastically processable biodegradable polyester amide, optionally in a mixture with one or more other thermoplastically processable biodegradable polymer components,
  at least one agrochemically active compound and
  optionally additives.

Furthermore, it has been found that the compositions according to the invention can be prepared by mixing
  a) at least one thermoplastically processable biodegradable polyester amide, optionally in a mixture with one or more other thermoplastically processable biodegradable polymer components,
    at least one agrochemically active compound and
    optionally additives
  and heating to a temperature between 50° C. and 180° C. and
  b) converting the resulting thermoplastically processable homogeneous mixture into mouldings or films by extrusion.

Finally, it has been found that the plant-treatment compositions according to the invention are highly suitable for applying agrochemically active compounds in agriculture, in forestry or in horticulture.

It is extremely surprising that the compositions according to the invention are considerably more suitable for applying agrochemically active compounds than the constitutionally most similar preparations of the prior art for the same purpose. It is also unexpected that the compositions according to the invention are stable in water and under moist and warm conditions.

The compositions according to the invention have a number of advantages. Thus, these preparations permit a continuous release of active compound over a prolonged period of time. By varying the rate of degradation of the polymer, the dose of active compound that is released can be adapted to the particular requirements. It is also favourable that the compositions according to the invention are sufficiently stable towards moisture, so that there is no risk of a premature release of active compound by hydrolytic decomposition. Finally, it is a particular advantage that the polymers acting as matrix are completely biodegradable under the conditions of application.

The plant-treatment compositions according to the invention contain one or more thermoplastically processable biodegradable polyester amides. These are to be understood as polymers of this type which have aliphatic ester groups and aliphatic amide groups and are compostable, i.e. which are completely degraded by the action of microorganisms, even under mild conditions.

Preference is given to polyester amides of this kind which have a random arrangement of the ester and amide segments and an average molecular weight of between 5000 and 100,000, preferably between 10,000 and 50,000, particularly preferably between 10,000 and 35,000, based on the number-average molecular weight.

Particular preference is given to polyester amides which are derived from monomers from the groups of the dialcohols, such as ethylene glycol, 1,4-butanediol, 1,3-propanediol, 1,6-hexanediol, diethylene glycol, etc., of the trialcohols, of the dicarboxylic acids, such as oxalic acid, succinic acid, adipic acid, etc., and/or their methyl, ethyl etc., esters, of the hydroxycarboxylic acids, such as lactic acid and the lactones, such as caprolactone etc., of the aminoalcohol, such as ethanolamine, propanolamine, etc., of the cyclic lactams, such as ε-caprolactam, laurolactam, etc., of the ω-aminocarboxylic acids, such as aminocaproic acid, etc., and/or of mixtures (1:1 salts) of dicarboxylic acids, such as adipic acid, fumaric acid, etc., and diamines, such as hexamethylenediamine, diaminobutane, etc. and/or of the hydroxyl- or acid-capped polyesters having molecular weights of between 200 and 10,000 as ester-forming component.

Very particular preference is given to polyester amides which are derived from cyclic lactams, such as ε-caprolactam, as amide-forming component and 1,4-butanediol and adipic acid as ester-forming components and have a proportion of ester between 30 and 80% by weight, preferably between 35 and 65% by weight, particularly preferably between 35 and 55% by weight.

The polyester amides can contain from 0.1 to 5% by weight, preferably from 0.1 to 2% by weight, of branching agents. Preferred branching agents are trifunctional alcohols, such as trimethylolpropane or glycerol, furthermore tetrafunctional alcohols, such as pentaerythritol, and also trifunctional carboxylic acids, such as citric acid.

The polyester amides contained in the plant-treatment compositions according to the invention are known or can be prepared by known methods (cf. EP-A 0 641 871).

Suitable co-components which may be contained in the polyester amides are customary thermoplastically processable and biodegradable polymers. Preference is given to polyesters, polyether esters, copolyesters, polyanhydrides, polyester urethane-ureas, polyester urethanes, thermoplastic polysaccharides or polysaccharide derivatives, and also to polyesters, polyether esters and polyester amides which contain aliphatic and aromatic ester groupings Particularly preferred co-components are polyesters, such as polylactide, polyglycolide, polycaprolactone, polyhydroxyalkoxides, polyaspartic acid and polytartrates, furthermore thermoplastic polysaccharides, such as cellulose esters, cellulose ethers, cellulose ether esters and starch derivatives, such as starch esters, and also thermoplastic starch.

The content of additional polymer components in the polyester amides can be varied within a relatively wide range, i.e., in general, between 1 and 80% by weight, preferably between 5 and 50% by weight.

The plant-treatment compositions according to the invention contain one or more agrochemically active compounds.

In the present context, agrochemically active compounds are to be understood as all substances which are customary for the treatment of plants. Fungicides, bactericides, insecticides, acaricides, nematicides, herbicides, plant-growth regulators and plant nutrients may be mentioned as being preferred.

The following are examples of fungicides:
2-aminobutane; 2-anilino-4-methyl-6-cyclopropyl-pyrimidine; 2',6'-dibromo-2-methyl -4'-trifluoromethoxy4'-trifluoromethyl-1,3-thiazole-5-carboxanilide; 2,6-dichloroN-(4-trifluoromethylbenzyl)-benzamide; (E)-2-methoxyimino-N-methyl-2-(2-phenoxyphenyl) -acetamide; 8-hydroxyquinoline sulphate; methyl (E)-2-{2-[6-(2-cyanophenoxy)-pyrimidin -4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, dichlofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, phthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metirarn, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforin, triticonazole, validamycin A, vinclozolin, zineb, ziram, 8-tert-butyl-2-(N-ethyl-N-n-propyl-amino)-methyl-1,4-dioxa-spiro-[4,5]decane, N-(R)-(1-(4-chlorophenyl)-ethyl)-2,2-dichloro-1-ethyl-3t-methyl-1r-cyclopropaiecarboxamide (mixture of diastercomers or individual isomers), 1-methylethyl [2-methyl-1-[[[1-(4-methylphenyl)-ethyl]-amino]-carbonyl]-propyl]-carbamate and N-(2,3-dichloro-4-hydroxy)-1-methyl-cyclohexyl-1-carboxanilide.

The following are examples of bactericides:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The following are examples of insecticides, acaricides and nematicides:

abamectin, acephate, acriathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5-(trifluoro-methyl)-1H-pyrrolo-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, chloethocarb, chlorethoxyfos, chlorfenvinphos, chlorfluazuron, chlormephos, N-[(6-chloro-3-pyridinyl)-methyl)]-N'-cyano-N-methyl-ethaneimideamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiophos, prothoate, pymetrozin, pyrachlophos, pyradaphenthion, pyresmethrin, pyrethrum, pyridaben, pyrimidifen, pyriproxifen, quinalphos, salithion, sebufos, silaflutofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

The following are examples of herbicides:

Anilides, such as, for example, diflufenican and propanil; arylcarboxylic acids, such as, for example, dichloropicolinic acid, dicamba and picloram; aryloxyalkanoic acids, such as, for example, 2,4-D, 2,4-DB, 2,4-DP, fluroxypyr, MCPA, MCPP and triclopyr; aryloxy-phenoxy-alkanoic esters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as, for example, chlortoluron, diuron, fluometuron, isoproturon, linuron and methabenzthiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromxynil, dichlobenil and ioxynil; oxyacetamnides, such as, for example, mefenacet; sulfonylureas, such as, for example, amidosulfuron, bensulfuron-methyl, chlorimuron-ethyl, chlorsulfuron, cinosulfuron, metsulfuron-methyl, nicosulfuron, primisulfiuron, pyrazosulfuron-ethyl, thifensulfuron-methyl, triasulfuron and tribenuron-methyl; thiolcarbamates, such as, for example, butylate, cycloate, diallate, EPTC, esprocarb, molinate, prosulfocarb, thiobencarb and triallate; triazines, such as, for example, atrazine, cyanazine, simazine, simetryne, terbutryne and terbutylazin; triazinones, such as, for example, hexazinone, metamitron and metribuzin; others, such as, for example, aminotriazole, beefuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Examples of plant growth regulators which may be mentioned are chlorocholine chloride and ethephon.

Examples of plant nutrients which may be mentioned are customary inorganic or organic fertilizers for providing plants with macro- and/or micronutrients.

Suitable additives which may be contained in the plant-treatment compositions according to the invention are all substances which are customarily used for such preparations. Preference is given to fillers, to plasticizers and stabilizers and to lubricants and glidants known from plastics technology.

The following are examples of fillers: sodium chloride, carbonates, such as calcium carbonate or sodium bicarbonate, furthermore aluminium oxides, silicas, aluminas, precipitated or colloidal silicon dioxide, and also phosphates.

The following are examples of lubricants and glidants: magnesium stearate, stearic acid, talc and bentonite.

Suitable plasticizers are all substances which are customarily used for this purpose for polyester amides.

Examples which may be mentioned are esters of phosphoric acid, esters of phthalic acid, such as dimethyl phthalate and dioctyl phthalate, and esters of adipic acid, such as diisobutyl adipate, furthermore esters of azelaic acid, malic acid, citric acid, maleic acid, ricinoleic acid, myristic acid, palmitic acid, oleic acid, sebacic acid. Stearic acid and trimellitic acid, and also complex linear polyesters, polymeric plasticizers and epoxidized soya bean oils.

Suitable stabilizers are antioxidants and substances which protect the polymers against undesirable degradation during processing.

Colorants which may be contained in the compositions according to the invention are all colorants which are customarily utilizable for plant-treatment compositions.

The concentrations of the individual components in the compositions according to the invention can be varied within a relatively wide range. Thus, the content

- of polyester amides, optionally in a mixture with additional polymer components, is generally between 60 and 99% by weight, preferably between 70 and 95% by weight,
- of agrochemically active compounds is generally between 1 and 30% by weight, preferably between 1 and 20% by weight and
- of additives is generally between 0 and 30% by weight, preferably between 0 and 20% by weight.

When carrying out the process according to the invention, in general, the desired amounts of the components are mixed with one another in any order and then heated, with stirring or kneading, to temperatures between 50° C. and 180° C., preferably between 60° C. and 160° C. The resulting paste-like mass or liquid mixture can then be converted into mouldings or films using the methods which are customary for thermoplastically processable polymers, with the aid of dies, presses or other suitable devices. In this context, mouldings are to be understood as rods, plates, fibres, bands, nets, granules or other mouldings. It is furthermore possible to grind the resulting products in the solid state to give powders. Moreover, it is possible to prepare culture containers for plants, such as pots or vats. Additionally, it is also possible to coat other substances with compositions according to the invention.

For carrying out the process according to the invention, all devices which are customary for processing thermoplastic materials are suitable. In general, the process is carried out in heatable mixers or kneaders and/or extruders.

The compositions according to the invention can be applied to the plants and/or their habitat as such or in the form of customary formulations prepared from them, such as granules, spray liquors, powders or pastes.

Thus, the compositions according to the invention can, for example, be used for incorporating agrochemically active compounds into the soil. To this end, they are, as depot preparations, incorporated into the soil in the vicinity of the roots of the plants to be treated, for example in the form of meals, dusts or granules, or they are inserted into the soil as rods, spheres, tablets or other mouldings.

The compositions according to the invention can also be employed for treating individual plants, such as, for example, trees. To this end, they are introduced into the sap stream of the plants, preferably in the form of suitable mouldings, such as rods, tablets, plates, films, tiles, tissues, strips, rivets, nails, clamps, bolts, needles, hollow nails or wires. For this purpose, the mouldings are either introduced into the plant in cavities which are prepared in an appropriate manner, or they are simply pushed, pressed or punched into the plant tissue. They can also be inserted under carefully detached bark or parts of plants, the bark or the parts of the plant subsequently being used for covering once again.

The compositions according to the invention can also be used for preparing transcuticular formulations. For this purpose, they are applied in the form of coatings, film-forming pastes, films, foils or plasters onto the surface of the plant.

The application rate of the compositions according to the invention can be varied within a relatively wide range. It depends on the particular active compounds and on their content in the compositions.

The invention is illustrated by the examples below.

PREPARATION EXAMPLES

Example 1 a) Preparation of polyester amide having a proportion of ester of 40% by weight from an acid-capped oligoester of adipic acid and butanediol and from ε-caprolactam. 565.8 g (5 mol) of ε-caprolactam, 292 g (2 mol) of adipic acid and 180 g (2 mol) of 1,4-butanediol are combined and slowly heated to 170° C. in an autoclave, under autogenous pressure. After a period of 3 hours, the autoclave is vented and water is distilled off. Depending on the intensity of the distillation, the mixture is heated to 220° C. and vacuum is applied. Towards the end, the polymerization is concluded using oil pump vacuum at 240° C. for 4 hours. A pale-yellow product is obtained which can be granulated. The melting point is 123° C., according to DSC. The relative viscosity (1% by weight strength in m-cresol at 25° C.) is 2.8.

The resulting biodegradable product is referred to hereinbelow as polyester amide I.

b) At a melt temperature of 130° C., 90 g of polyester amide I and 10 g of imidacloprid are kneaded at 50 rpm in a kneader for 30 minutes. This gives a homogeneous, thermoplastically formable material which is processed in a heatable press at 150° C. to give a film having a thickness of 1 mm, and small plates having the dimensions 10×10×1 mm are cut from this film.

Example 2

At a melt temperature of 130° C., 95 g of polyester amide I and 5 g of imidacloprid are kneaded at 50 rpm in a kneader for 30 minutes. This gives a homogeneous, thermoplastcally formable material which is processed in a heatable press at 150° C. to give a film having a thickness of 1 mm, and small plates having the dimensions 10×10×1 mm are cut from this film.

Example 3

At a melt temperature of 130° C., 90 g of polyester amide 1 and 5 g of 2,6-dichloro-benzonitrile are kneaded at 50 rpm in a kneader for 30 minutes. This gives a homogeneous, thermoplastically formable material which is processed in a heatable press at 150° C. to give a film having a thickness of 1 mm, and small plates having the dimensions 10×10×1 mm are cut from this film.

Example 4

At a melt temperature of 130° C., 90 g of polyester amide I and 5 g of tebuconazole are kneaded at 50 rpm in a kneader for 30 minutes. This gives a homogeneous, thermoplastically formable material which is processed in a heatable press at 150° C. to give a film having a thickness of 1 mm, and small plates having the dimensions 10×10×1 mm are cut from this film.

Examples 5 to 9

The amounts of starch and glycerol stated in the table below are initially charged in a kneader and, at a melt temperature of 100–140° C., kneaded for 5 minutes. The amounts of polyester amide I and imidachloprid stated in the table below are subsequently added, and the mixture is kneaded at 50 rpm, in each case for 30 minutes at 140° C. In each case, this gives a homogeneous, thermoplastically formable material which is processed in a heatable press at 150° C. to give a film having a thickness of 1 mm from which small plates having the dimensions 10×10×1 mm are cut.

TABLE 1

| Example No. | Imidacloprid % by weight | Polyester amide I % by weight | Starch % by weight | Glycerol % by weight |
|---|---|---|---|---|
| 5 | 5 | 89.5 | 5 | 0.5 |
| 6 | 5 | 84 | 10 | 1 |
| 7 | 5 | 73 | 20 | 2 |
| 8 | 5 | 51 | 40 | 4 |
| 9 | 5 | 29 | 60 | 6 |

USE EXAMPLES

Example A

Using the HPLC method, the content of active compound in the small plates described in Example 2 is determined. The content detected is 48 mg of imidacloprid per gram.

One of these small plates is added to water, and the water is stirred at a rate of 1 rps at 20° C. At intervals of in each case 24 hours, the content of active compound in the water is determined using the HPLC method. It is found that more than 95% of the imidacloprid has been released after 192 hours.

Example B

Small plates according to Example 2 are added to compost and left there at 37° C. for 7 days. The content of released imidacloprid is then determined. It is found that 76% of the imidacloprid has been released.

Example C

Small platelets according to Example 2 are added to compost which is not microbially active (poisoned) and left there at 37° C. for 7 days. The content of released imidacloprid is then determined. It is found that 10% of the imidacloprid has been released.

Example D

Small plates according to Example 3 are ground by customary methods with cooling. The ground material is analytically examined for its 2,6-dichlorobenzonitrile content.
2,6-Dichlorobenzonitrile content
 before grinding: 5.3% by weight
 after grinding: 4.0% by weight.
At room temperature, 3 g of the ground material are exposed to an airstream of 400 liters over a period of 3 days. The granules are then analyzed for their content of 2,6-dichlorobenzonitrile; it is 3.8% by weight. Consequently, 5% of the 2,6-dichlorobenzonitrile has been released.

COMPARATIVE EXAMPLES

Comparative Example 1

90 g of biodegradable polylactide (Cargill) and 5 g of imidacloprid are, at a melt temperature of 150° C., kneaded at 50 rpm in a kneader for 30 minutes. This gives a homogeneous, thermoplastically formable material which is processed in a heatable press at 140° C. to a film having a thickness of 1 mm from which small plates having the dimensions 10×10×1 mm are cut.

Using the HPLC method, the content of active compound in these small plates is determined. The content detected is 48 mg of imidacloprid per gram.

One of these small plates is added to water, and the water is stirred at a late of 1 rps at 20° C. At intervals of in each case 24 hours, the content of active compound in the water is determined using the HPLC method. It is found that even after 288 hours, no imidacloprid has been released.

Comparstive Example 2

One of the small plates described in Comparative Example 1 is added to water, and the water is stirred at 40° C. at a rate of 1 rps. At intervals of in each case 24 hours, the content of active compound in the water is determined using the HPLC method. It is found that even after 168 hours, no imidacloprid has been released.

Comparative Example 3

One of the small plates described in Comparative Example 1 is added to water, and the water is stirred at 60° C. at a rate of 1 rps. At intervals of in each case 24 hours, the content of active compound in the water is determined using the HPLC method. It is found that, after 168 hours, 18% of the imidacloprid has been released.

Comparative Example 4

Small plates according to Comparative Example 1 are added to compost and left there at 37° C. for 7 days. The content of released imidacloprid is then determined. It is found that 4% of the imidacloprid has been released.

Comparative Example 5

Small platelets according to Comparative Example 1 are added to compost which is not microbially active (poisoned) and left there at 37° C. for 7 days. The content of released imidacloprid is then determined. It is found that 4% of the imidacloprid has been released.

Comparative Example 6

The surface of granules having the same particle size as the ground material described in Example D is coated with 5% by weight of 2,6-dichlorobenzonitrile. At room temperature, 3 g of this ground material are exposed to an airstream of 400 liters over a period of 3 days. The granules are then analyzed for their content of 2,6-dichlorobenzonitrile; it is 3.5% by weight. Consequently, 30% by weight of the 2,6-dichlorobenzonitrile has been released.

What is claimed is:
1. Plant-treatment compositions consisting of
   at least one thermoplastically processable biodegradable polyester amide, optionally in a mixture with one or more other thermoplastically processable biodegradable polymer components,
   at least one agrochemically active compound and
   optionally additives.
2. Composition according to claim 1, characterized in that the polyester amides contained therein have an average molecular weight of between 5000 and 100,000.
3. Compositions according to claim 1, wherein the polyester amides are derived from materials selected from the group consisting of:
   dialcohols,
   trialcohols, dicarboxylic acids and their esters,
hydroxycarboxylic acids,
lactones,
aminoalcohols
cyclic lactams,
ω-aminocarboxylic acids,
mixtures (1:1 salts) of dicarboxylic acids and diamines,
hydroxyl- or acid-capped polyesters having molecular weights of between 200 and 10,000, and
mixtures thereof.

4. Compositions according to claim 1, wherein the polyester amides are derived from monomers selected from the group consisting of:
cyclic lactams,
1,4-butanediol and adipic acid and have a proportion of ester of between 30 and 80% by weight.

5. Compositions according to claim 1, characterized in that thermoplastically processable biodegradable polyesters, polyether esters, copolyesters, polyanhydrides, polyester urethane-ureas, polyester urethanes, thermoplastic polysaccharides and/or polysaccharide derivatives are contained therein as co-components.

6. Compositions according to claim 1, characterized in that thermoplastically processable biodegradable polyesters, polyether esters and/or polyester amides which have aliphatic and aromatic ester groups are contained therein as co-components.

7. Compositions according to claim 1, wherein the agrochemically active compounds are selected from the group consisting of fungicides, bactericides, insecticides, acaricides, nematicides, herbicides, plant-growth regulators and plant nutrients.

8. Compositions according to claim 1, characterized in that imidacloprid is contained therein as agrochemically active compound.

9. Process for preparing compositions according to claim 1, comprising the steps of:
  a) mixing at least one thermoplastically processable biodegradable polyester amide, optionally in a mixture with one or more other thermoplastically processable biodegradable polymer components, and with at least one agrochemically active compound optionally with additives;
  b) heating the mixture in step a) to a temperature between 50° C. and 180° C.; and
  c) converting the resulting thermoplastically processable homogeneous mixture into mouldings or films by extrusion.

* * * * *